(12) United States Patent
Blackburn et al.

(10) Patent No.: US 7,816,098 B2
(45) Date of Patent: Oct. 19, 2010

(54) METHODS OF MAKING AND USING A PROTEIN ARRAY

(75) Inventors: Jonathon Michael Blackburn, Cambridge (GB); John David Sutherland, Cheshire (GB); Mitali Samaddar, Cambridge (GB); Michelle Ann Mulder, Cambridge (GB); Roland Z. Kozlowski, Cambridge (GB)

(73) Assignee: Sense Proteomic Limited, Babraham, Cambridge (GB)

( * ) Notice: Subject to any disclaimer, the term of this patent is extended or adjusted under 35 U.S.C. 154(b) by 857 days.

(21) Appl. No.: 09/967,321

(22) Filed: Oct. 1, 2001

(65) Prior Publication Data

US 2003/0118994 A1    Jun. 26, 2003

Related U.S. Application Data

(63) Continuation of application No. PCT/GB01/00395, filed on Jan. 31, 2001.

(60) Provisional application No. 60/196,490, filed on Apr. 12, 2000.

(51) Int. Cl.
*G01N 33/00* (2006.01)

(52) U.S. Cl. .................................................. 435/7.92

(58) Field of Classification Search .................. 435/4, 435/6, 7.1, 7.8–7.95, 7.4, 7.2, 287.1–287.3; 436/512, 536, 538, 540, 543, 544–548, 518
See application file for complete search history.

(56) References Cited

U.S. PATENT DOCUMENTS

| | | | | |
|---|---|---|---|---|
| 4,865,974 A | * | 9/1989 | Ben-Bassat et al. | 435/68.1 |
| 5,741,645 A | * | 4/1998 | Orr et al. | 435/6 |
| 5,861,250 A | * | 1/1999 | Stanley et al. | 435/6 |
| 5,914,241 A | * | 6/1999 | Valkirs | 435/7.4 |
| 5,916,810 A | | 6/1999 | Jarvik | 435/440 |
| 6,197,599 B1 | * | 3/2001 | Chin et al. | 436/518 |
| 6,218,131 B1 | * | 4/2001 | Keesee et al. | 435/7.23 |
| 6,350,853 B1 | * | 2/2002 | Nielsen et al. | 530/300 |
| 6,387,628 B1 | * | 5/2002 | Little et al. | 435/6 |
| 6,503,184 B1 | * | 1/2003 | Ni et al. | 514/12 |
| 6,593,120 B1 | * | 7/2003 | Riggs et al. | 435/194 |
| 6,610,839 B1 | * | 8/2003 | Morin et al. | 536/24.1 |
| 6,673,914 B1 | * | 1/2004 | Hoon | 536/23.5 |

FOREIGN PATENT DOCUMENTS

| | | |
|---|---|---|
| WO | WO 99/11777 | 3/1999 |
| WO | WO 99/39210 | 8/1999 |
| WO | WO 99/45130 | 9/1999 |
| WO | WO 99/51773 | 10/1999 |
| WO | WO 00/04382 | 1/2000 |
| WO | WO 01/04265 | 1/2001 |
| WO | WO 01/57198 | 8/2001 |

OTHER PUBLICATIONS

Pandey, A. and Mann, M., "Proteomics to study genes and genomes," *Nature* 405:837-846, Nature Publishing Group (Jun. 2000).
Strausberg, R.L. and Finley Austin, M.J., "Functional genomics: technological challenges and opportunities," *Physiological Genomics* 1:25-32, American Physiological Society (Jul. 1999).

* cited by examiner

*Primary Examiner*—Ann Y Lam
(74) *Attorney, Agent, or Firm*—Mintz Levin Cohn Ferris Glovsky and Popeo P.C.; Ivor R. Elrifi; David E. Johnson

(57) ABSTRACT

The present invention describes methods for the preparation of protein arrays of full length proteins. The use of such arrays in screening methods is also described.

21 Claims, 5 Drawing Sheets

Figure 1A:
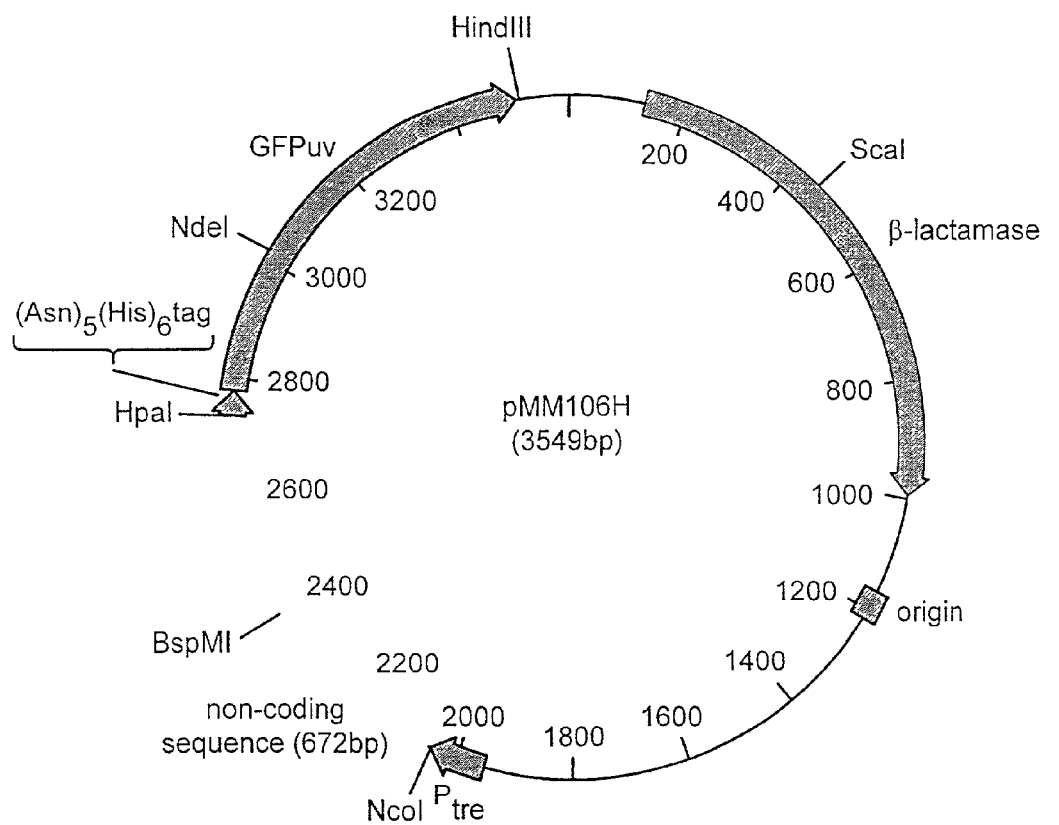

Grow individual colonies in liquid culture and induce expression.

Lyse cells and add Ni$^{2+}$-NTA coated magnetic beads to crude lysate

Nickel-nitrilotriacetic acid (NTA)

NTA-Ni$^{2+}$

Wash beads to remove other proteins

NTA-Ni$^2$

Measure enzymatic activity on beads 1-chloro-2, 4-dinitrobenzene

Glutathione + → Glutathione S transferase → $\lambda_{max}$ = 340nm

METHODS OF MAKING AND USING A PROTEIN ARRAY

The present application is a continuation of International Application PCT/GB01/00395, filed Jan. 31, 2001, and published in English as WO 01/57198 A2 on Aug. 9, 2001, which claims priority benefit to Great Britain applications GB 0002215.2, filed Jan. 31, 2000 and GB 001988.7, filed Aug. 11, 2000; and to U.S. Provisional Patent Application No. 60/196,490, filed Apr. 12, 2000. The fill disclosure of each of these applications is herein incorporated by reference.

The present invention relates to novel methods of generating protein expression arrays, as well as the use of such arrays in rapid screening.

The genome mapping projects are revolutionising the therapeutic target discovery process and with it the drug discovery process. As new therapeutic targets are identified, high throughput screening of existing and combinatorial chemical libraries will suggest many potential lead compounds which are active against these targets. It will clearly be uneconomic to pursue all lead compounds through even early phase clinical trials; currently however no rapid method exists for evaluating such lead compounds in terms of their likely activity profiles against all proteins in an organism. If available, such a method would allow the potential toxicology profiles of all the lead compounds to be assessed at an early stage and this information would significantly enhance the process of deciding which lead compounds to pursue and which to set aside.

There is a complementary need in the pharmaceutical industry to identify all the targets of existing drugs (either in the market already or still in development) and hence to define their mechanism of action. The availability of such information will greatly facilitate the process of gaining regulatory approval for new drugs since it is increasingly clear that the regulatory bodies now regard a knowledge of the mechanism of action to be of paramount importance. In addition, this type of information would enable the design of improved second generation drugs. This follows because the majority of drugs have at least minor side effects, which probably result from binding of the drug or a metabolite thereof to undesirable targets; all of these target proteins need to be identified in order to define the criteria necessary for design of improved drugs. Currently however no simple method exists to generate this information and a number of potential multi-million dollar drugs fall by the wayside simply for lack of knowledge of the target of action.

Protein-protein interactions are being increasingly recognised as being of critical importance in governing cellular responses to both internal and external stresses. Specific protein-protein interactions therefore represent potential targets for drug-mediated intervention in infections and other disease states. Currently the yeast two-hybrid assay is the only reliable method for assessing protein-protein interactions but in vivo assays of this type will not be readily compatible even in a non-high throughput format with the identification of specific agonists or antagonists of protein-protein interactions. Functional proteome expression arrays, or "proteome chips", will enable the specificity of protein-protein interactions and the specificity of any drug-mediated effect to be determined in an in vitro format. They will therefore have enormous potential because they will simply revolutionise this area of research.

One way in which functional proteome arrays could be generated is to individually clone, express, purify and immobilise all proteins expressed in the specific proteome. Here though, an important initial consideration concerns the absolute size of the genome of interest together with considerations about the availability of sequence data for the entire genome. By way of illustration of these points, a typical bacterial genome is ~5 Mbp and a small number have now been completely sequenced (for example *Helicobacter pylori, Escherichia coli*, and *Mycobacterium tuberculosis*); fungal genomes are typically ~40 Mbp, mammalian genomes at ~3 Gbp and plant genomes at ~10 Gbp. Current estimates are that the human genome sequence will be finished around 2003, although how much of this information will be in the public domain is very much open to question. Clearly it will be completely impractical to expect that the genomes of anything other than representative model organisms will become available in a realistic time frame, yet from the perspective of functional proteomics, model organisms are of only limited value. So, whilst in principle within the next four years it may be possible to design and synthesise primers to clone each of the ~100,000 genes in the human genome from cDNA libraries, in practice this will be both enormously expensive (the cost of primers alone would run in to several millions of dollars) and a hugely laborious process, even if the necessary sequence data is available.

But what about those pharmaceutically relevant organisms for which the complete sequence data will not be available? These cannot be simply ignored by functional proteomics so what are the alternatives? Expression cDNA libraries could in principle be used together with non-specific immobilisation to create an array of proteins, but this technology is significantly limited by the fact that non-specific immobilisation is usually associated with loss of function because the fold of the protein is disrupted. In addition, all host cell proteins will also be immobilised which will at best markedly reduce signal-to-noise ratios and at worst result in obfuscation of positive results. The ability to create a functional proteome array in which individual proteins are specifically immobilised and purified via a common motif or tag without affecting function and without requiring knowledge of the entire genome sequence would therefore represent a huge advance in the field of functional proteomics.

We have now developed a novel approach which solves the problems described above by providing methodology which allows each protein in a proteome to be tagged with a common marker at a defined position within the protein without requiring any prior knowledge of the DNA sequence of the corresponding genes. This 'tag' can then be used to impart a commonality and specificity to downstream immobilisation and purification procedures, which in turn enables the creation of spatially defined arrays in which many thousands of proteins from a given proteome are displayed.

An important consideration here relates to the precise positioning of the 'tag'. If the tag is inserted in-frame in to any gene but at an undefined, random position, the likelihood is that the resultant tagged protein will be truncated in an undefined manner and in the majority of cases correct folding, and hence function, will be destroyed. The methodology described here circumvents this problem by inserting the tag immediately after the start codon or immediately before the stop codon of any given gene such that the individual full-length, tagged proteins fold correctly and hence retain function when specifically immobilised in the array.

Since each protein in the array will be fully functional, the arrays can then be screened directly to identify the targets of drugs and other biologically relevant molecules. The spatial definition of the arrays will allow the phenotype of each protein to be related directly to its genotype to allow the identification of 'hits'.

Thus, in a first aspect, the present invention provides a method of generating a protein array, which comprises cloning and expressing one or more proteins as full length proteins which are each tagged at either the N- or C-terminus with a marker moiety.

The marker moiety can be either a peptide sequence, eg a hexa-histidine tag, an antibody epitope or a biotin mimic, or indeed a complete protein, or protein domain, eg the maltose binding protein domain. The marker moiety itself can be post-translationally modified, eg by addition of a biotin or lipid molecule. In a preferred embodiment, the marker moiety would also allow purification of "tagged" proteins.

Thus, the methods of the present invention allow the specific modification, in one pot, of every member of a cDNA library in a manner which does not rely on any knowledge of the sequence of individual genes. Instead it is based on the common start or stop codon in all genes. The modification will be in the form of a precise insertion, in frame, of additional known sequence DNA either immediately following the start codon or immediately preceding the stop codon of each cDNA as required.

The additional DNA will encode a known marker moiety, which will be in the same reading frame as each individual cDNA product. Each genetically modified cDNA produced according to the methods of the present invention will thus encode an individual protein which now has a common moiety, eg a polypeptide, "tag" fused precisely to either its N- or C-terminus. Since every member of a cDNA library will be modified in precisely the same manner, the net result will be that every protein encoded by the cDNA library will now be tagged with a common moiety at either their N- or C-termini.

In general, the proteins expressed from the cDNA library will be "tagged" and can be readily identified and isolated. Once purified they can be attached to microarrays, for example. Attachment can be effected by means of the tag itself, or alternatively, by means of another moiety which is first attached to the proteins.

Arrays formed by the methods described herein form a second aspect of the invention.

Such arrays comprise the "tagged" protein expression library, immobilised, usually on a solid support. The skilled person will understand that a range of possible solid supports are in comon usage in the area of arrays and any of these "substrates" can be utilised in the production of arrays of the present invention.

As discussed herein, the methods of the present invention allow tagging of all proteins in a given proteome specifically at either the N- or C-terminus. Whilst some proteins may not tolerate N-terminal extensions and others might not tolerate C-terminal extensions, it is likely that the vast majority of proteins will tolerate one or other such extensions. Existing library cloning methods, however, simply cannot address this problem since they clone genes either as full-length, unmodified cDNAs or as random and almost inevitably truncated fusions to some protein partner.

Compared to the latter, the present methods allow precise, full-length cDNA libraries to be created as fusions to, eg a desired peptide partner. Compared to the former, the method of immobilising proteins in an array as described herein is through specific rather than non-specific interactions, and these specific interactions are a function of the tag added to the termini of each cDNA. Additionally, the methods described herein can be used to screen purified, immobilised proteins which have been expressed in non-bacterial host organisms to aid maintenance of function through correct folding and post-translational modification, whereas existing methods such as phage display or λ-cDNA expression libraries are restricted to bacterial hosts in which the majority of eukaryotic proteins are found to be synthesised in a non-functional form, either due to mis-folding or incorrect post-translational modification.

The methods of the present invention have a wide range of potential in vitro applications which can be broadly divided into three main areas. These are the study of protein-ligand interactions, the study of protein-protein interactions, and the study of protein-DNA interactions.

Protein-Ligand Interactions

The methods described herein will allow the rapid profiling of the interactions between a given new chemical entity and all proteins in a given proteome. This can be achieved simply through probing the appropriate proteome array with the NCE at varying stringencies in what might be considered a reverse high throughput screen. The readout from such a screen will be directly useful in many situations, some of which are described below.

High throughput screening programs in which libraries of compounds are tested against cells or whole organisms often identifies leads which give rise to a phenotypic change without the target being known prior to screening. Subsequent identification of the primary target can, however, be a very laborious process. The methods of the present invention can be applied directly to this type of problem since it will be possible to create a functional proteome array for the species concerned and then screen this array with the lead compound to identify which proteins within the proteome it is targeting. This massively parallel approach to identifying protein-ligand interactions will greatly speed up and simplify the determination of primary targets of NCEs, and will also allow identification of weaker secondary interactions which may also be important. In addition, the methods can be applied directly to the question of species cross-reactivity, allowing a potential antifungal compound, for example, to be quickly assessed in terms of its interactions with, for example, all proteins in a human proteome; this type of information is likely to prove very useful in any subsequent optimisation of lead compounds.

High throughput screening methods now allow the rapid identification of small molecules which bind to a given protein which has itself previously been identified as a potential therapeutic target. However, these methods do not address the question of how selective any given interaction might be yet this knowledge is potentially crucial in deciding whether to pursue a given lead compound or not; perceived wisdom would argue that compounds which target single poteins are likely to show fewer side effects than those which also hit a large number of related or unrelated proteins.

There are a number of examples of compounds which have progressed successfully through third phase clinical trials yet have failed to win regulatory approval because their primary mechanism of action is not known. The antidepressant drugs mianserin and trazadone and the Pfizer anti-arthritic drug tenidap are examples here, each representing hundreds of millions of dollars investment for no return. The methods described herein can potentially be applied to the resurrection of such failed drugs since if the primary targets of such drugs can be discovered and subsequently verified in terms of mechanism of action, the vastly expensive clinical trial data is already in place for regulatory approval.

All existing drugs have side effects, to a greater or lesser extent, an example here being the otherwise attractive anti-schizophrenia drug clozapine. If the molecular origin of such side effects could be determined, this would greatly facilitate the design of future generation drugs with optimised primary effects combined with minimised side effects. Again the presently described methods can be applied directly to such problems since in creating a profile of the interactions between a compound and all proteins in a proteome, aberrant secondary interactions will be identified and these can subsequently be assessed in terms of whether they are linked to known side effects.

The methods of the present invention can also be used to identify families of proteins, such as serine proteases, through screening proteome arrays with generic inhibitors. This would then allow the subsequent development of biochips displaying, for example, all human serine proteases or, alternately, all kinases or all p450 enzymes for more focused screening of lead compounds. A p450 biochip, for example, would have utility in assessing whether a given lead compound is likely to be metabolised or not, since p450-mediated hydroxylation is often the first step in this process and is thought to be one of the primary sources of patient-to-patient variability in drug response; indeed one of the goals of drug design now is to generate compounds which are not metabolised in the first place and here again a p450 chip would have significant potential utility.

Protein-protein interactions

Protein-protein interactions and multiprotein complexes are of critical importance in cellular biology. Signalling pathways, for example, are commonly initiated by an interaction between a cell surface receptor and an external ligand, and this is followed by a cascade of protein-protein interactions which ultimately result in the activation of a specific gene. Individual protein-protein interactions might be dependent on the presence of a specific ligand or alternatively might be blocked by a specific ligand, whilst some multiprotein complexes will only form in a ligand-dependent manner.

Thousands of new protein-protein interactions have been identified using two-hybrid technologies. The methods described herein overcome the limitations of such methods and can be used to screen proteome arrays with individual labelled proteins to identify not only interacting partners but also the relative strengths of individual interactions. The methods can also be applied to the identification of the components of multiprotein complexes, even where their assembly is ligand dependent.

An example of the use of the methods in this way in defining novel protein-protein interactions would be the identification of the signalling partners of the cytosolic domain of a particular cell surface receptor which has been implicated in a disease state; identification of such signalling partners would be directly relevant from a pharmaceutical perspective since such protein-protein interactions might immediately represent possible therapeutic targets.

Protein-DNA Interactions

It has been estimated that roughly 10% of all genes in the human genome encode transcription factors yet only a small percentage of these are at present identified. The binding of specific transcription factors to DNA enhancer elements, often in response to external stimuli, is a prerequisite for the formation of enhanceosome complexes which then switch on gene expression. There are various points at which gene expression can in principle be affected by drug administration: a drug might block the binding of a protein or small molecule to a cell surface receptor and hence block the signalling cascade at the beginning; a drug might block a protein-protein interaction or inhibit an enzymatic activity within the signalling cascade; or alternatively, a drug might block formation of specific protein-DNA or protein-protein interactions within the enhanceosome complex. As an example here, the transcription factor NF-κB is involved in cellular processes as diverse as immune and inflammation responses, limb development, septic shock, asthma, and HIV propeptide production. The majority of the intracellular signalling cascades in NF-κB activation are common to all these process so do not represent viable targets for intervention. The differences between the responses therefore lie in either the original ligand-receptor interaction or in the formation of specific enhanceosome complexes. NF-κB is known to bind to at least 14 different enhancer elements and the enhanceosome complexes therefore represent potential therapeutic targets. However, delineation of an individual enhanceosome complex requires knowledge of both the number of individual DNA-binding proteins involved and also their protein-protein interactions with each other. The present methods can be used to directly address both these questions. A proteome array can be screened with specific DNA probes to identify novel DNA binding proteins, Alternatively, the proteome array can be screened with the transactivation domain of a given transcription factor to identity other proteins with which it interacts. Cross correlation of such screens should allow identification of new components of specific enhanceosome complexes.

The protein arrays generated by the methods of the present invention will also allow the selection of molecules, which recognise each protein displayed in the arrays. In a preferred embodiment, the selected molecules will be antibodies or antibody-like proteins and will be displayed on phage or on ribosomes or will be covalently linked to the encoding mRNA.

Thus, a phage displayed antibody library can be applied to each immobilised protein in the array and non-binding antibodies removed by washing. The selected phage can then be recovered and used to infect bacteria according to normal procedures. The phage-infected bacteria can then produce either phage particles displaying the selected antibodies for further rounds of selection, or they can produce soluble antibody fragments for direct use. The terms 'antibody' or 'antibody fragments' here refer to single chain Fvs, FAB fragments, individual light or heavy chain fragments, derived from mouse, human, camel or other organisms.

In a preferred embodiment, the protein array will be in microwell format such that after the selection step, the phage particles can be recovered by addition of appropriate bacterial cells to each well where they will become infected by the selected phage particles. Growth media can then be added to each well and the infected bacteria allowed to grow and express the antibody fragments, whilst maintaining the physical separation of the antibody fragments selected to each immobilised protein in the array. If so desired, new phage particles produced by the infected bacteria can be used in subsequent rounds of selection. Such procedures are now routine for selecting polyclonal or monoclonal antibody fragments to a single purified and immobilised protein. In effect then the original protein arrays here will allow the generation of polyclonal or monoclonal antibody fragments to thousands of correctly folded proteins in a massively parallel manner whilst otherwise using standard in vitro antibody selection methods.

The selected, solubly expressed antibody fragments from each well of the original array can themselves be immobilised in to a new spatially defined array such that the antibody fragments in each position of the new array were selected against the proteins immobilised in a single, defined position in the original array. The antibody arrays so-generated will contain at each position either polyclonal or monoclonal antibody fragments, depending on the number of rounds of selection carried out prior to immobilisation of the soluble antibody fragments.

Such antibody arrays will have a number of potential uses including capture of individual proteins from a crude cell or tissue lysate for differential expression monitoring of the relevant proteome. Alternatively, the antibody-captured proteins might be screened directly for ligand-binding function. In general, any one monoclonal antibody might bind to the target protein so as to block its function, but another monoclonal antibody might bind but not block function. In a massively parallel approach, it is clearly impractical to assess all monoclonal antibodies to all proteins in a proteome individually for their ability to bind but not affect function. A polyclonal set of antibodies to all proteins in a proteome however is likely to contain individual antibodies which have the desired ability to bind but not affect function and will, in addition, contain individual antibodies which recognise all post-translational modifications of a given protein. Thus in general, polyclonal rather than monoclonal antibody arrays generated as described will likely be advantageous for screening captured proteins directly for function.

Compared to the original protein arrays, the antibody arrays created by the methods described here will have the advantage that all proteins immobilised on the array will be stable under similar conditions. The proteins captured from the crude cell or tissue lysate will not be recombinant but will have been naturally expressed. Moreover, the captured proteins can be screened for function or ligand binding etc directly after capture from the crude cell or tissue lysate, which should aid maintenance of function.

Thus, in further aspects, the present invention provides:
(i) a method of screening one or more compounds for biological activity which comprises the step of bringing said one or more compounds into contact with a protein array as defined herein and measuring binding of the one or more compounds to the proteins in the array;
(ii) a method of screening one or more proteins for specific protein-protein interactions which comprises the step of bringing said one or more proteins, eg a cell surface receptor, into contact with an array as defined herein, and measuring binding of the one or more specific proteins with the proteins of the array;
(iii) a method of screening one or more proteins for specific protein-nucleic acid interactions which comprises the step of bringing said one or more nucleic acid probes into contact with an array as defined herein and measuring binding of the probes to the proteins in the array;
(iv) the use of an array as defined herein in the rapid screening of a compound, protein or nucleic acid;
(v) the use of an array as defined herein in screening for molecules which recognise each protein in the array, wherein the molecules are preferably antibodies;
(vi) a method of generating an antibody array which comprises bringing a protein array, as defined herein, into contact with an antibody library, such that one or more proteins in the protein array bind to at least one antibody in the antibody library, removing any unbound antibodies and immobilisation of those antibodies bound to proteins in the protein array; and
(vii) a method for the screening of protein function or abundance which comprises the step of bringing an antibody array as defined herein into contact with a mixture of one or more proteins.

The methods (i), (ii), (iii) and (vi) may also include the step of first providing the array according to one or more of the methods of the present invention.

Preferred features of each aspect of the invention are applicable to each other aspect, mutatis mutandis.

The present invention will now be described with reference to the following examples, which should not in any way be construed as limiting the scope of the invention.

Figure 1B:
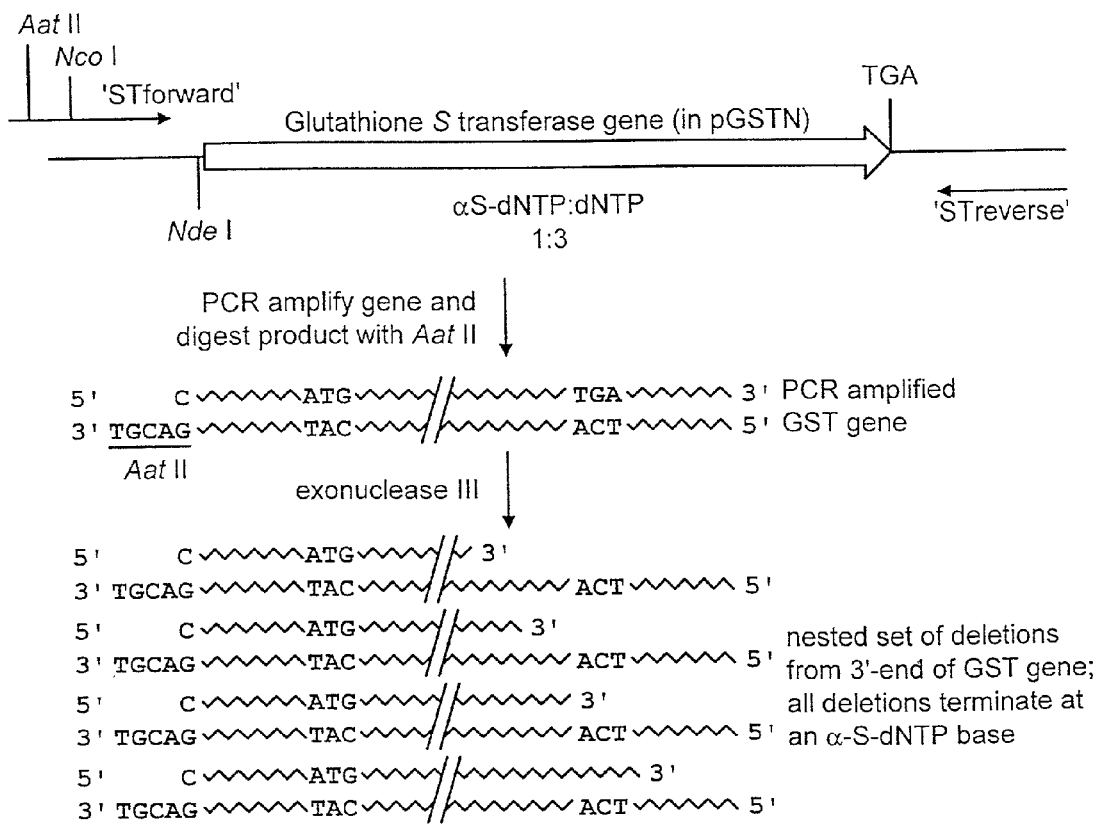
Figure 1C:
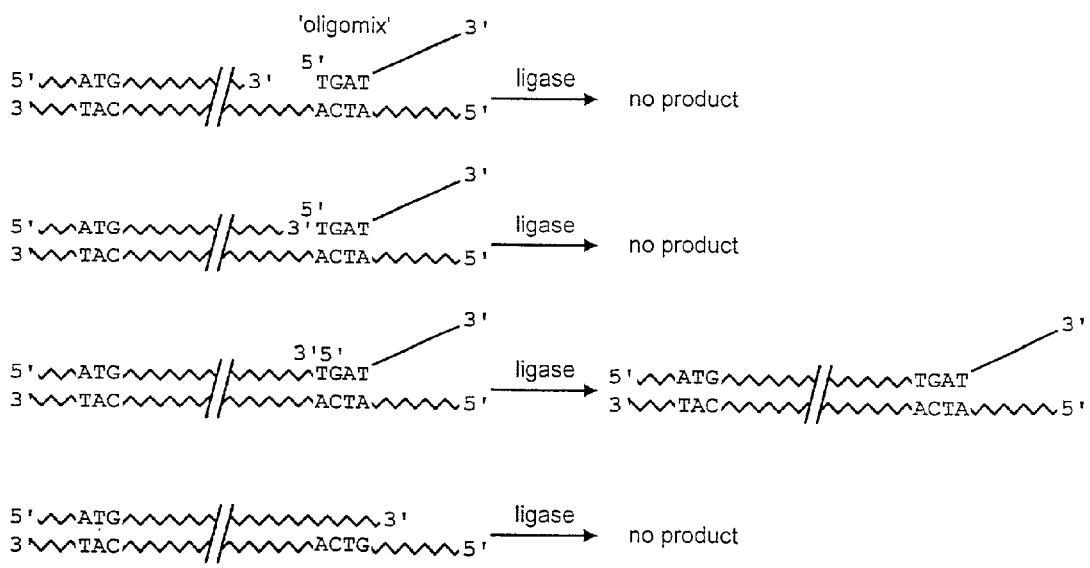
Figure 1D:
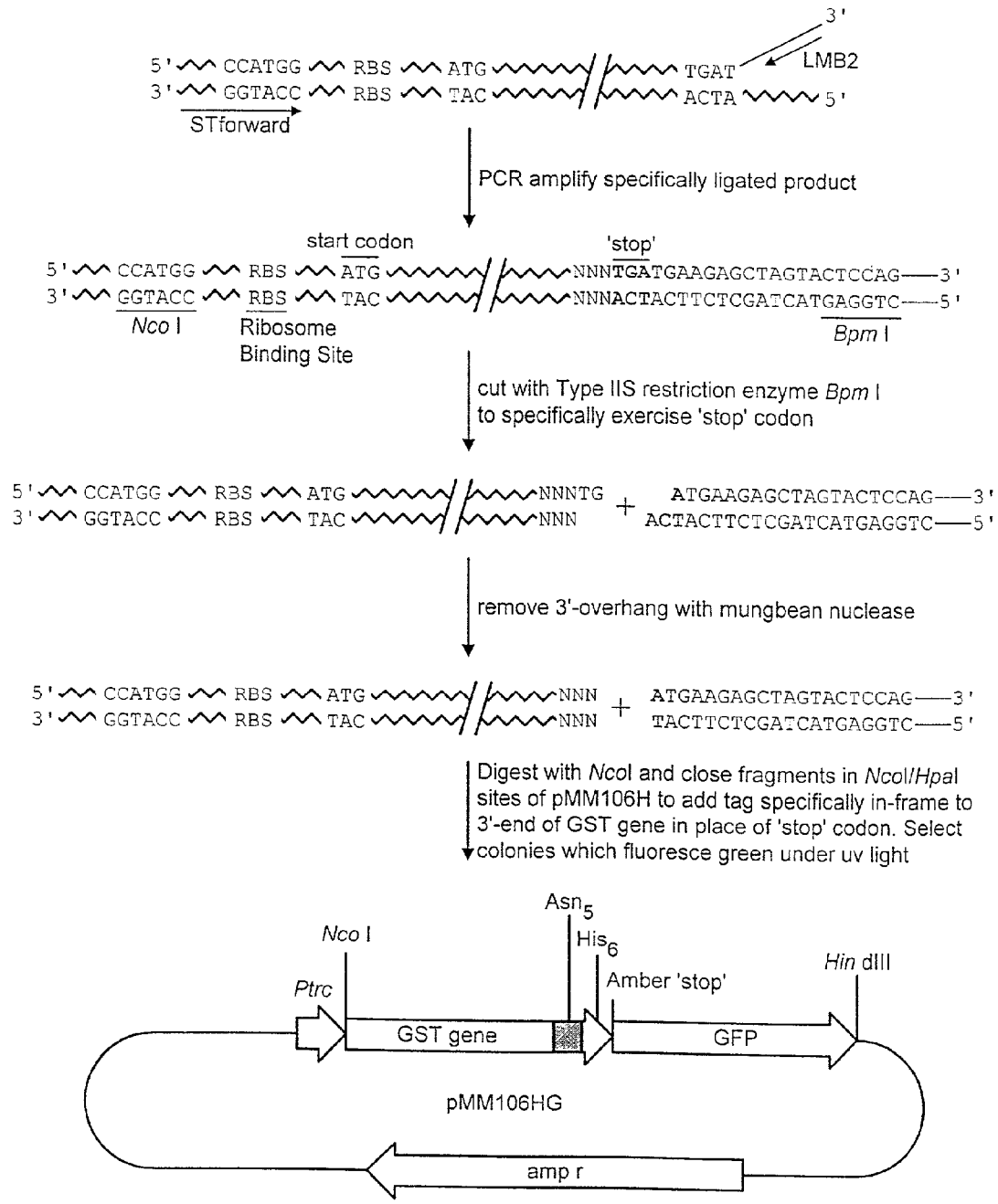

FIG. 1a: shows the construction of the vector pMM106H;

FIG. 1b: shows details of the PCR amplification and exonuclease digestion of an example gene (GST) prior to tagging;

FIG. 1c: shows details of the specific ligation and PCR amplification to introduce the tag;

FIG. 1d: shows details of the cloning of the PCR products; and

Figure 1E:
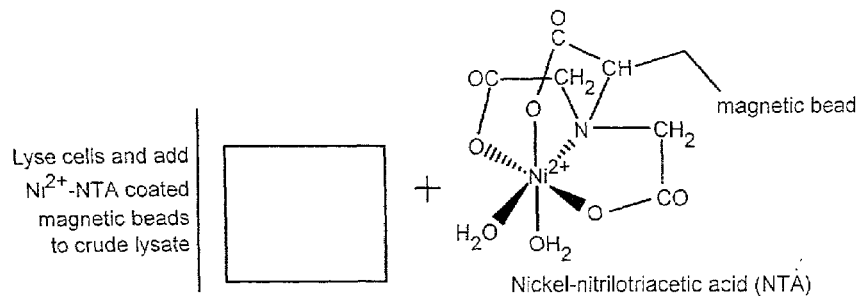
Figure 1E:
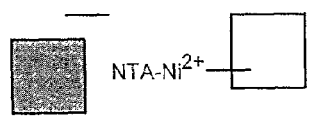
Figure 1E:
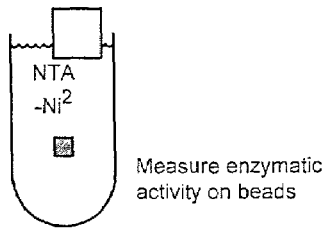
Figure 1E:
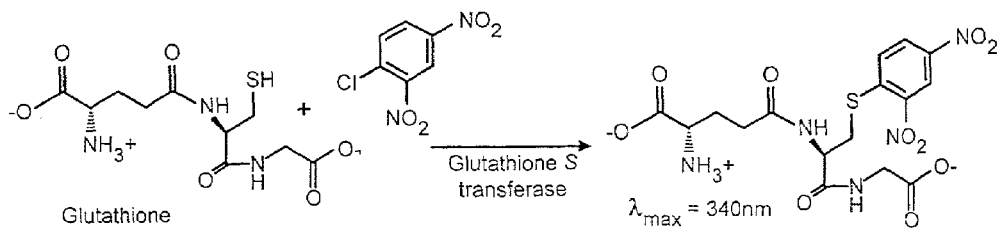

FIG. 1e: shows the reaction between Glutathione and 1-chloro-2,4-dinitrobenzene catalysed by GST.

EXAMPLE 1

(a) Vector Construction (See FIG. 1a)

We have constructed a vector pMM106H derived from pUC19 which contains a strong hybrid promoter (Ptrc) to drive the expression of genes cloned into an Nco I site immediately downstream of the promoter sequence. We inserted a 676 bp nonsense DNA sequence as a stuffer fragment between the Nco I site and a downstream Hpa I site. Hpa I is a blunt-end cutter and is positioned to cleave the vector such that the downstream DNA encodes a polyasparagine, hexahistidine peptide if the reading frame is on the first base of the blunt-end. Following the hexahistidine tag is an amber stop codon (TAG) followed by the gene encoding the green fluorescent protein (GFP) of the jellyfish *Aequorea victoria*. Genes cloned into pMM106H as Nco I/blunt-end fragments result in fusions to the His-tag and GFP only if the correct reading frame is created at the Hpa I site during cloning. GFP is used here as a reporter gene to facilitate visual screening of clones expressing the His tag, while also providing an indication of the correct folding of the fusion protein, since GFP is only active when folded into the correct conformation. The amber stop codon will result in a small amount of the full length fusion protein for visualisation of green colonies, while most of the fusion protein will terminate immediately after the His tag and can be used for subsequent immobilisation and enzyme assays. The construction of pMM106H was confirmed by sequencing.

We constructed a second vector pGSTN by first PCR-amplifying the *Schistosoma japonicum* glutathione S transferase (GST) gene from pGEX-2T (Pharmacia) under standard conditions using primers 'GSTfwd2' (5'-ATG CTG CAG ACG TCA ACA GTA TCC ATG GCC CCT ATA CTA GG-3') (SEQ ID NO: 1) and 'GSTHindIII' (5'-GCG AGG AAG CTT GTC AAT CAG TCA CGA TGA ATT CCC G-3') (SEQ ID NO: 2). These primers introduce an Nco I restriction site at the start codon of GST, mutate the second residue of GST from serine to alanine, and introduce a stop codon in the multiple cloning site 3'- of the GST gene followed by a Hin dIII restriction site. The PCR product was then cloned under standard conditions as an Nco I/Hin dIII fragment into pTrcHisA (Invitrogen) previously digested with Nco I/Hin dIII to generate pGSTN.

(b) PCR Amplification and Exonuclease Digestion of Genes Prior to Tagging (See FIG. 1b)

We amplified the GST gene from the construct pGSTN using the polymerase chain reaction with custom-designed vector-specific primers 'STforward' (5'-ATG CTG ACG TCA TGA GGC CCA TGG GGC CCG GAT AAC AAT TTC ACA CAG G-3') (SEQ ID NO: 3) and 'STreverse'(5'-GCG GAT CCT TGC GGC CGC CAG GCA AAT TCT GTT T-3') (SEQ ID NO: 4) which bind to the vector 156 bp upstream of the start and 84 bp downstream of the stop codons respectively. 30 cycles of PCR (94° C. 1 min; 57° C. 1 min; 72° C. 2 min) were carried out in four separate 100 µl reactions. Each PCR reaction contained ~20 ng template DNA, 50 pmol each primer and 2.5 units Pwo polymerase. Each PCR reaction was carried out in a standard buffer (10 mM Tris.HCl pH8.8, 25 mM KCl, 5 mM $(NH_4)_2SO_4$, 2 mM $MgSO_4$, 10% DMSO). Each of the four PCR reactions then also contained a non-standard deoxynucleotide triphosphate mix, as follows:

Reaction 1) 200 µM dATP, 200 µM dTTP, 200 µM dCTP, 150 µM dGTP, 50 µM α-S-dGTP;
Reaction 2) 200 µM dATP, 200 µM dTTP, 200 µM dGTP, 150 µM dCTP, 50 µM α-S-dCTP;
Reaction 3) 200 µM dATP, 200 µM dGTP, 200 µM dCTP, 150 µM dTTP, 50 µM α-S-dTTP;
Reaction 4) 200 µM dGTP, 200 µM dTTP, 200 µM dCTP, 150 µM dATP, 50 µM α-S-dATP.

The inclusion of a single α-thio deoxynucleotide triphosphate in each specific PCR mix results in a random but statistical incorporation of the relevant α-S-dNTP into the specific final PCR product. The four individual PCR mixes were then pooled, and purified using a QIAquick PCR cleanup kit (Qiagen), under standard conditions, and digested to completion with the restriction enzyme Aat II. The resulting ~1000 bp PCR products were then gel-purified.

5 µg of the digested PCR product was then incubated with 375 Units of Exonuclease III for 45 minutes at 37° C. in a 50 µl reaction. The Exo III digestion was carried out in a standard reaction buffer (66 mM Tris.HCl pH8.0, 6.6 mM $MgCl_2$, 5 mM DTT, 50 µg/ml bovine serum albumin). These conditions ensure that digestion by Exo III has reached completion. The enzyme was then inactivated by heating to 75° C. for 15 minutes. The product of the Exo III digestion is a nested set of deletions from the 3'-end of the PCR product; the 5'-end of the PCR product is protected from digestion since restriction with Aat II leaves a 3'-overhang which is then resistant to Exonuclease III activity.

Exonuclease III is, a non-processive 3'- to 5'-exonuclease which is unable to hydrolyse α-thio-containing nucleotides so in the present protocol, every time Exo III reaches an α-thio-deoxynucleotide base, the progressive truncation of the recessed 3'-end of the PCR product is halted. The net result is thus a nested set of deletions as a consequence of the random incorporation of each α-S-dNTP at the earlier stage. The ratio of α-S-dNTP to dNTP used in the original PCR amplifications was determined empirically such that the envelope of nested deletions spanned a 400 bp window of sizes centred approximately 100 bp shorter than the original full length PCR product. We confirmed this by taking a portion of the Exo III mix and treating the nested deletions with mung bean nuclease. This process removed the 5'- and 3'-overhangs to yield blunt-end products which were then sized on 1% agarose/TBE gels, using a 100 bp DNA ladder as a standard.

Clearly a number of different 3' to 5' nuclease activities could be used for generating the requisite set of nested 3'-recessed deletions in the procedure described above; these include but are not restricted to Exonuclease III, *E. coli* DNA polymerase I, T4 DNA polymerase, T7 DNA polymerase.

(c) Specific Ligation and PCR Amplification to Introduce Tag (See FIG. 1*c*)

5 µl of the Exo III reaction mix was diluted into T4 DNA ligase buffer in the presence of a roughly 25-fold molar excess of an 'oligo mix'. The 'oligo mix' consists of either one of 2 different pools of oligonucleotides. The first pool, "oligomixA", contains 12 oligonucleotides in which each of the three possible stop codons are represented at the 5' end, followed immediately by a degenerate base. The remaining region of each of the oligos is the same in all 12 cases and is effectively random sequence except for two Type IIS restriction enzyme sites (Sap I and Bpm I) followed by a complementary recognition sequence for the primer 'LMB2' (5'-GTA AAA CGA CGG CCA GT-3') at the 3'-end. The sequences of the 12 oligos are as follows:

```
5'-TAA GGA AGA GCT AGT ACT CCA GAC TGG CCG TCG TTT TAC-3'
(SEQ ID NO: 5)

5'-TAA AGA AGA GCT AGT ACT CCA GAC TGG CCG TCG TTT TAC-3'
(SEQ ID NO: 6)

5'-TAA TGA AGA GCT AGT ACT CCA GAC TGG CCG TCG TTT TAC-3'
(SEQ ID NO: 7)

5'-TAA CGA AGA GCT AGT ACT CCA GAC TGG CCG TCG TTT TAC-3'
(SEQ ID NO: 8)

5'-TAG GGA AGA GCT AGT ACT CCA GAC TGG CCG TCG TTT TAC-3'
(SEQ ID NO: 9)

5'-TAG AGA AGA GCT AGT ACT CCA GAC TGG CCG TCG TTT TAC-3'
(SEQ ID NO: 10)

5'-TAG TGA AGA GCT AGT ACT CCA GAC TGG CCG TCG TTT TAC-3'
(SEQ ID NO: 11)

5'-TAG CGA AGA GCT AGT ACT CCA GAC TGG CCG TCG TTT TAC-3'
(SEQ ID NO: 12)

5'-TGA GGA AGA GCT AGT ACT CCA GAC TGG CCG TCG TTT TAC-3'
(SEQ ID NO: 13)

5'-TGA AGA AGA GCT AGT ACT CCA GAC TGC CCG TCG TTT TAC-3'
(SEQ ID NO: 14)
```

```
5'-TGA TGA AGA GCT AGT ACT CCA GAC TGG CCG TCG TTT TAC-3'
(SEQ ID NO: 15)

5'-TGA CGAAGAGCT AGT ACTCCAGAC TGG CCG TCG TTT TAC-3'
(SEQ ID NO: 16)
        Sap I           Bpm I      LMB2 binding site
```

The second pool, "oligomixB", consists of 3 sets of oligonucleotides, each with one of the 3 stop codons represented at the 5' end, followed immediately by 6 degenerate residues. The remaining region of each of the oligos is the same in all 3 sets and contains two Type IIS restriction enzyme sites (Bpm I and Bse RI) followed by a complementary recognition sequence for the primer 'LMB2' at the 3'-end. The sequences of the 3 sets of oligos are as follows:

```
5'-TAA NNN NNN ACT CCT CCT CCA GAC TGG CCG TCG TTT TAC-3'
(SEQ ID NO: 18)

5'-TAG NNN NNN ACT CCT CCT CCA GAC TGG CCG TCG TTT TAC-3'

5'-TGA NNN NNN ACTCCTCCTCCAGAC TGG CCG TCG TTT TAC-3'
(SEQ ID NO: 19)
            Bse RI     Bpm I     LMB2 binding site
```

The Exo III mix plus either oligomixA or oligomixB were annealed for 30 minutes at 16° C. and then 400 Units of T4 DNA ligase were added after which the reaction was incubated overnight at 16° C. The ligation products were purified using a QIAquick PCR cleanup kit (Qiagen) under standard conditions and used as template in a standard PCR reaction using Pwo polymerase with primers 'STforward' and 'LMB2'. 30 cycles of PCR (94° C., 1 min; 57° C. 1 min; 72° C. 2 min) were carried out to generate PCR products ranging up to 1000 bp.

Both oligomixA and oligomixB are able to anneal competitively to the single-stranded DNA regions of the original template exposed by the Exo III hydrolysis of one strand of the duplex carried out in the previous step. Subsequent to annealing, successful ligation between any oligo and the template requires that the oligo be annealed with absolute complementarity at its 5'-end and, additionally, that the recessed 3'-residue of the duplex template directly abuts the 5'-residue of the specifically annealed oligo. PCR using one primer which binds to the newly ligated oligo and a second primer which binds at the 5'-end of the duplex template then selectively and specifically amplifies only those duplexes which have undergone such a ligation. The 5'-end of each of the 12 oligos in oligomixA corresponds to a stop codon and so, of the 12 oligos contained in this mix, only one can anneal with absolute complementarity at its 5'-end to the four base pair recognition sequence comprising the first in-frame stop codon of GST and the base immediately 3'- of the stop codon, as shown in FIG. 1c. The remaining 11 oligos might anneal perfectly at their 5'-ends elsewhere within the nested set of deletions but these other specific annealing events can only occur at out-of-frame stop codons within the GST gene or at stop codons downstream of the first in-frame stop codon. Wherever a newly annealed oligo directly abuts the 3'-recessed residue of the duplex template, ligation can occur. PCR at this stage will therefore amplify not only the exact, full-length gene but also a set of truncated and extended products. The oligos in oligomixB are expected to react in the same way. The 5' end of each of the 3 sets of oligos in the pool corresponds to a stop codon, followed by 6 residues which are effectively random. Therefore, the pool will contain one permutation in which the stop codon and the next 6 residues perfectly match those downstream of the gene of interest. This oligo will bind with a higher specificity than the corresponding oligo from the 12 oligo pool, since the complementarity stretches over 9 nucleotides as opposed to 4.

The theoretical difference between oligomixA and oligomixB lies in the sequence immediately following the stop codon at the 5'-end of each oligo. In oligomixA, a single degenerate base is then followed by a single nonsense, but defined DNA sequence so it is possible that this defined region could bias the annealing of the oligomix in favour of individual 'stop' codons (whether in-frame or out-of-frame) within any given gene by providing unintentional but nevertheless additional base pair complementarity beyond the four designed base pairing interactions at the 5'-end of each oligo. Any bias in annealing might be manifested downstream in a bias towards clones in which specific excision and replacement of an individual stop codon (whether in-frame or out-of-frame) had occurred. Such a bias in the frequency of modification at different stop codons might be undesirable and oligomixB is designed to circumvent this as follows. Any given stop codon within an individual gene or library will be followed immediately by a defined, but unknown, sequence. All three stop codons are represented within oligomixB and each is immediately followed by all possible hexanucleotide sequences (i.e. by a random hexamer sequence) such that for any given stop codon within a gene or library, there will be one oligo in oligomixB which will match the stop codon and its precise downstream sequence exactly, resulting in 9 base pairs of complementarity overall. Since this will be true for all stop codons, oligomixB should therefore not suffer from any bias of the type which might be possible with oligomixA.

We have found the overall process of Exo III digestion, annealing and ligation of the oligomixes, and specific PCR amplification to be highly reproducible. As controls in this procedure we have shown that if any one of Exonuclease III, T4 DNA ligase, or either oligomix is omitted we obtain absolutely no PCR product. This demonstrates that the process is highly selective.

It will also be appreciated that T4 DNA ligase could be substituted by a number of different DNA ligases, for example Taq DNA ligase or Tsc DNA ligase, which might show different specificities.

(d) Variations on Procedure

Clearly a number of different 3' to 5' nuclease activities could be used for generating the requisite set of nested 3'-recessed deletions in the procedure described above; these include but are not restricted to Exonuclease III, *E. coli* DNA polymerase I, T4 DNA polymerase, T7 DNA polymerase.

An obvious variation on the original procedure for producing full-length inserts with the stop codon or start codon precisely removed involves the production of a nested set of 5'-recessed deletions in a PCR product which spans the coding sequence. This could potentially be carried out using nucleases such as λ exonuclease, *E. coli* DNA polymerase I, Taq DNA polymerase, T7 gene 6 exonuclease. Thus for example the original PCR product could be digested with λ exonuclease, which removes nucleotides from one strand of dsDNA in a 5' to 3' direction. Since the enzyme only recognises 5'-phosphate groups as substrates, one of the two strands can be protected by incorporating a 5'-hydroxyl group at the end of the appropriate primer in the initial PCR amplification. A nested set of deletions can thus be created as described above for exonuclease III, except that the opposite strand is digested to leave 5'-recessed termini. A mixture of oligos in which the complement of the stop codon is represented at the 3'-end of the oligo, immediately preceded by 6 randomised residues and before that by a defined sequence encoding a Type IIS restriction site can then be annealed to the exposed single strand regions. One oligo from the mixture will specifically anneal to each exposed stop codon and will serve as a primer for *E. coli* DNA polymerase I, which polymerises in the 5' to 3' direction, digesting the strand ahead of it with it's 5' to 3' exonuclease activity. This new duplex DNA fragment can then be specifically amplified using a primer which binds to the 5'-end of the original PCR product and one which binds specifically to the newly annealed and extended oligo. In this procedure, the 3' end of the annealed oligo is not required to directly abut the 5'-recessed residue of the duplex template. Oligos from the mixture can anneal to any complementary region on the exposed single stranded DNA template in a manner akin to random hexamer priming, but importantly, strand extension will only occur where the 3'-end has annealed with absolute complementarity and the 3'-ends of the oligos in the mixture are designed to be complementary to stop codons only. Thus, only when the 3'-end of an oligo has bound specifically to the matching stop codon will primer extension and subsequent PCR amplification occur. Binding to out-of-frame stop codons and those downstream of the true stop codon of the gene of interest will also occur, resulting in the PCR amplification of not only the exact, full-length gene but also a set of truncated and extended products.

(e) Cloning and Analysis of the PCR Products (See FIG. 1*d*)

PCR products (~5 μg) ranging in size from 800 to 1000 bp were cleaned up using a QIAquick PCR purification kit (Qiagen) and then digested to completion with the Type IIS restriction enzyme Bpm I. This enzyme cuts remotely but specifically 14 bases away from its recognition sequence in one strand and 16 bp on the other strand leaving a 3'-recessed end. This restriction modification thus specifically excises from the PCR product the stop codon at which the 5'-end of an individual oligo from the 'oligo mix' annealed and successfully ligated in the previous step.

The recessed 3'-ends of the digested products were then removed using mung bean nuclease under standard conditions to generate a blunt-end at the 3'-end of the PCR products. The DNA was purified using a QIAquick PCR purification kit (Qiagen) under standard conditions and subsequently digested to completion with the restriction enzyme Nco I. The restricted DNA fragments ranging from 800 bp to 1000 bp were then purified on a 1% agarose/TBE gel using a QIAquick gel extraction kit (Qiagen). The vector pMM106H (3 μg) was digested to completion with the restriction enzymes Nco I and Hpa I and the 2870 bp backbone fragment was gel purified. The vector DNA and the restricted PCR products were then ligated together under standard conditions and the ligation mix was used to transform *E. coli* DH5α cells which were then recovered and plated onto LB plates containing 100 μg/ml carbenicillin.

This cloning procedure was carried out on the full set of PCR products obtained in the previous step. However, only the PCR product derived from the specific annealing and ligation of an oligo to the first in-frame stop codon should be able to give rise to in-frame fusions to the hexahistidine tag and GFP after cloning steps via this procedure; all other PCR products cloned in this manner should only lead to out-of-frame fusions to the hexahistidine tag and GFP. This follows because ligation of the blunt end of the PCR product to the blunt end of the vector results in a genetic fusion in which the translation reading frame of the downstream vector DNA is dictated by the original reading frame of the excised stop codon. If the stop codon was out-of-frame with respect to the GST gene, the newly appended hexahistidine-coding sequence will also be out-of-frame with respect to the GST gene, whilst if the stop codon was in-frame with the GST gene, the newly appended hexahistidine-coding sequence will also be in-frame with respect to the GST gene. However, only those PCR products in which the specifically excised stop codon was the first in-frame stop codon of GST can give rise to hexahistidine-(and GFP-) tagged GST fusion protein when the DNA is transcribed and translated. The only hexahistidine-(and GFP-) tagged proteins which can arise from the overall specific process described above will therefore necessarily be full-length GST fusions to the polyasparagine, hexahistidine tag.

Colonies obtained from the cloning procedure described above were visualised at 365 nm to identify green fluorescent colonies. Ninety colonies (both white and green) were picked at random, replica-plated and analysed by colony Western blot under standard conditions using anti-His-tag and anti-GST antibodies. The anti-His-tag antibody will only bind to colonies which express a hexahistidine-tagged protein so the Western blot gives direct information about the number of colonies expressing in-frame fusions to the hexahistidine-tag. The anti-GST antibody, on the other hand, binds close to the C-terminus of the GST protein and therefore only recognises colonies expressing full- or nearly full-length GST proteins. We identified those colonies containing protein which was positively recognised by both anti-His-tag and anti-GST antibodies. The DNA from these colonies was amplified, purified and sequenced. The sequencing data confirmed the presence of two perfect in-frame fusions to full length GST, i.e. clones in which the first in-frame stop codon of the original GST gene had been specifically excised and replaced by an in-frame polyasparagine, hexahistidine tag. The rate of successful modification we obtained via this overall procedure is therefore approximately 2.2%. Both of the positive clones were found to fluoresce green upon exposure to long wavelength ultraviolet light, due to the expression of sufficient amounts of the full-length GST-hexahistidine-GFP fusion. In all further experiments, therefore, only green fluorescent colonies were picked for further analysis by Western blot. We have found that approximately 70-80% of green fluorescent colonies express protein recognised by the anti-His-tag antibody. It is likely that in the remaining 20-30% of cases, translation is initiating on the first ATG of the GFP gene, independently of the hexahistidine tag, possibly with the aid of a pseudo-ribosome binding site introduced by the cloned insert.

We have amplified, purified and sequenced plasmid DNA from green fluorescent colonies expressing protein recognised by both the anti-His-tag and anti-GST antibodies. For inserts prepared using both oligomixA and oligomixB, the rate of successful modification was found to be approximately 25% of all green colonies. Use of the GFP gene as a marker for in-frame fusions therefore increases the efficiency of detecting the correct clones approximately 10-fold.

It will also be appreciated that Mung Bean Nuclease could be substituted by a number of different single strand nucleases, for example S1 nuclease or RNaseT, which might show different specificities and that a number of different suitably positioned Type IIS Restriction enzymes could be used in place of BpmI, for example SapI.

(f) Immobilisation and Functional Analysis of Tagged Proteins (See FIG. 1e)

E. coli DH5α cells were transformed with one of the full-length, hexahistidine-tagged GST plasmids created via the above methodology. A single carbenicillin-resistant colony was grown to mid-log phase in 10 ml liquid culture and then supplemented with 100 μM IPTG to induce expression of the hexahistidine-tagged GST. After growth for a further 4 hours, cells were harvested and lysed by freeze-thaw/lysozyme. SDS-PAGE of the crude lysate showed an overexpressed protein at the expected size (27 kDa), which represented roughly 20% of total soluble protein, as well as a small amount of the 54 kDa GST-hexahistidine-GFP fusion, generated through amber suppression. The crude lysate (500 μl; 100 μg) was then mixed with Nickel-NTA magnetic beads (50 μl; binding capacity 15 μg hexahistidine-tagged protein) and the beads recovered by sedimentation under a magnetic field. The supernatant was discarded and the beads were washed and then resuspended in a glutathione S transferase assay buffer containing 1 mM each of glutathione and 1-chloro-2, 4-dinitrobenzene. End point assay data was collected after 30 minutes at room temperature by measuring the absorbance at 340 nm; this wavelength corresponds to the $\lambda_{max}$ of the product of the GST-catalysed reaction.

As controls, cultures of DH5α containing either the parent vector (pMM106H) or a plasmid encoding an unrelated His-tagged protein (alanine racemase) were grown, induced, harvested, lysed and assayed in parallel. GST activity was only detected on the beads which had been mixed with the crude lysate containing the His-tagged GST, clearly demonstrating that the observed GST activity was due specifically to the immobilised His-tagged GST and moreover that the protein retained activity on specific immobilisation.

After completion of the enzymatic assay, protein was eluted from the magnetic beads by addition of buffer containing 100 mM imidazole and analysed by SDS-PAGE. This showed that the sample which gave the positive activity assay result contained a single immobilised protein of the exact size expected for glutathione S transferase (27 kDa), thus confirming that the observed activity on the beads was due to this recombinant His-tagged protein alone.

EXAMPLE 2

(a) Modification, Immobilisation, and Assay of GST Using Two Different Tags

Following the procedure as described in Example 1 for modifying glutathione-S-transferase with a hexahistidine tag, we have demonstrated that the procedure is independent of the precise nature of the tag being added.

First, two further vectors were constructed which were identical to pMM106H except that the 676 bp Nco I/Hpa I nonsense DNA stuffer fragment was replaced by a 300 bp Nco I/Hpa I fragment derived from the *Escherichia coli* gdhA gene and the hexahistidine tag was replaced by either the FLAG peptide (an epitope tag) or the Strep II tag (which binds specifically and with a high affinity to streptavidin). These vectors have been designated pMM104F and pMM104S respectively. These vectors (3 μg of each) were separately digested to completion with Nco I and Hpa I and the 2870 bp backbone fragments were gel purified and ligated to the GST fragments generated from oligomixA as described in Example 1. Using a combination of anti-FLAG and anti-GST antibodies followed by sequencing, clones were identified that contained perfect in-frame fusions of the full length GST gene to the FLAG tag. Similarly using a combination of anti-GST antibodies and a streptavidin-horseradish peroxidase conjugate followed by sequencing, clones were identified that contained perfect in-frame fusions of the full length GST gene to the Strep II tag. In both examples, the frequency with which full-length, in-frame fusions were found was the same (within experimental error) as determined in Example 1.

These clones were used in immobilisation experiments, essentially as described in Example 1, except that the immobilisation substrates were anti-FLAG antibody-coated 96 well plates and streptavidin-coated magnetic beads respectively. As in Example 1, we have been able to demonstrate the specific immobilisation of the fusion proteins via these tags, and in addition we have been able to show that the GST fusion retains its activity when immobilised through either the FLAG or Strep tag.

EXAMPLE 3

(a) Modification of a Second Protein Using the Hexahistidine Tag

Following the procedure as described in Example 1 for glutathione-S-transferase, we have demonstrated that the procedure is independent of the precise gene being manipulated.

Thus starting with a plasmid encoding human transcription factor NF-κB p50 and following exactly the procedure described in Example 1 (using oligomixA) unless otherwise specified, we have been able to demonstrate the modification of NF-κB p50 such that the first in-frame stop codon has been specifically excised and replaced by an in-frame fusion to DNA encoding a polyasparagine, hexahistidine tag. Colony Western blots using an anti-His-tag antibody allowed identification of clones expressing hexahistidine-tagged protein. The DNA from these colonies was amplified, purified and sequenced. The sequencing data confirmed several clones encoded perfect in-frame fusions to full length NF-κB, i.e. clones in which the stop codon has been specifically excised and replaced by an in-frame hexahistidine tag. The frequency with which full-length, in-frame fusions was found in the case of NF-κB p50 was 1.1%, which is close to, and within experimental error of, that determined in Example 1 for GST.

(b) Immobilisation and Functional Analysis of Hexahistidine-tagged NF-κB p50

E. coli DH5α cells were transformed with one of the full-length, hexahistidine-tagged NF-κB plasmids created via the above methodology. A single carbenicillin-resistant colony was grown to mid-log phase in 10 ml liquid culture and then supplemented with 100 μM IPTG to induce expression of the hexahistidine-tagged NF-κB p50. After growth for a further 4 hours, cells were harvested and lysed by sonication. SDS-PAGE of the crude lysate showed an overexpressed protein at the expected size (38 kDa), which represented roughly 5% of total soluble protein, as well as a small amount of the 65 kDa NF-κB p50-hexahistidine-GFP fusion, generated through amber suppression.

```
κB motif
5'-CGT ATG TTG TGG GGA ATT CCC AGC GGA TAA C-3'
(SEQ ID NO: 20)

3'-GCA TAC AAC ACCCCTTAAGGG TCG CCT ATT G-5'
(SEQ ID NO: 21)
           NF-κB P50 binding site
```

A duplex oligonucleotide, 'κB motif', which contains a palindromic binding site for NF-κB p50, was labelled at the 3'-bases with digoxigenin using 3-terminal transferase under standard conditions (Boeliringer Mannheim).

The protein lysates were prepared using the lysozyme/freeze-thaw method in PBS (phosphate buffered saline pH 7.5) containing 5 mM β-mercaptoethanol. 200 µl of the soluble protein lysate from each clone, was applied to the Ni-NTA coated microwell and incubated at room temperature for 45 minutes. At the end of the incubation period, the wells were washed three times with PBST (PBS containing 0.02% Triton X-100) to remove all the unbound proteins. The wells were washed three times with DNA binding buffer (10 mM Tris.HCl pH 7.4, 75 mM KCl containing 5 mM β-mercaptoethanol with a soak time of 1 minute. The 3' digoxigenin labelled κB motif (2 pmol) was added to the wells in 200 µl of the DNA binding buffer containing 1 µg of poly (dI-dC) non-specific DNA. After another 30 minutes incubation the unbound DNA was removed by washing the wells three times with 10 mM Tris.HCl pH 7.4, 25 mM KCl containing 0.02% Triton X-100. An anti-digoxigenin antibody-alkaline phosphatase conjugate was diluted to 150 mU/ml in 'antibody dilution buffer' (10 mM Tris.HCl pH7.4, 25 mM potassium chloride) supplemented with 0.2% bovine serum albumin. The diluted antibody (200 µl) was then applied to the microwells. After 30 minutes at room temperature, unbound antibody was removed by washing the microwells with 'antibody dilution buffer' (3×350 µl) supplemented with 0.02% Triton X-100. 200 µl of a buffer (100 mM Tris.HCl pH9.5, 100 mM NaCl, 50 mM $MgCl_2$) containing 250 µM p-nitrophenyl phosphate (pNPP), an alkaline phosphatase substrate, was then added to the wells and the reaction allowed to proceed overnight at room temperature, after which the yellow colouration in each well (corresponding to formation of the product, p-nitrophenol) was quantitated at 405 nm. The background rate of hydrolysis of the substrate pNPP was low so a positive assay result was therefore immediately clear from the appearance of yellow colour in the wells. As controls in this assay we omitted either the crude lysate, or the labelled oligonucleotide, or the antibody, or added a 20-fold excess of unlabelled duplex oligo or replaced the hexahistidine-tagged NF-κB p50 containing crude lysates with equivalent amounts of a crude cell lysate from DH5α cells expressing hexahistidine-tagged GST in the same vector background.

In this assay, NF-κB p50 first binds to the labelled oligonucleotide via the specific binding site. The protein-DNA complex is then immobilised in the microwells via the hexahistidine tag and all other proteins (including complexes between the labelled oligo and other DNA binding proteins present in the crude lysate) together with any unbound, labelled oligo, are then washed away. Since the antibody-conjugate recognises the label on the oligo, not the hexahistidine-tagged protein, a positive signal in the assay can only be observed if the NF-κB p50-DNA interaction is maintained on immobilisation of NF-κB p50 via the tag; if this interaction is not maintained, the oligo will be lost during the washing steps so no colour change will be observed.

We found that the yellow product was only detected in the microwells which had contained the hexahistidine-tagged NF-κB p50 crude lysate and the digoxigenin-labelled oligonucleotide and to which the anti-digoxigenin antibody-alkaline phosphatase conjugate had been added. This demonstrated that the observed colour change was due specifically to the immobilised NF-κB p50-oligonucleotide complex and moreover that NF-κB p50 retained activity on specific immobilisation.

EXAMPLE 4

An alternative procedure for producing full-length genes or cDNAs with the stop codon precisely removed involves the production of a strand-specific nested set of 5'-recessed deletions in a PCR product which spans the coding sequence. This could potentially be carried out using any 5'- to 3'-exonuclease such as λ exonuclease, E. coli DNA polymerase I, Taq DNA polymerase, or T7 gene 6 exonuclease. Once the nested set of 5'-recessed deletions has been created, an oligo mix can be annealed to the exposed single strand regions; this oligo mix consists of a set of oligos in which the complement of each stop codon is represented at the 3'-end, immediately preceded by 6 randomised residues and before that by a defined sequence encoding a Type IIS restriction site and a complementary recognition sequence for the primer 'LMB2' (see Example 1). The sequence of the oligo set is thus as follows:

```
5'-GTA AAA CGA CGG CCA GTC TGG AGG AGG AGA NNN NNN TCA-3'
(SEQ ID NO: 22)

5'-GTA AAA CGA CGG CCA GTC TGG AGG AGG AGA NNN NNN TTA-3'
(SEQ ID NO: 23)

5'-GTA AAA CGA CGG CCA GTC TGG AGG AGG AGA NNN NNN CTA-3'
(SEQ ID NO: 24)
```

One oligo from the mixture will specifically anneal to each stop codon exposed on the sense strand and will serve as a primer for DNA polymerases having either strand displacing activity, such as Taq polymerase, or 5'- to 3'-exonuclease activity, such as E. coli DNA polymerase I. The newly generated duplex DNA fragment can then be specifically amplified using a primer which binds to the 5'-end of the original PCR product and one which binds specifically to the newly annealed and extended oligo. In this procedure, the 3' end of the annealed oligo is not required to directly abut the 5'-recessed residue of the duplex template. Oligos from the mixture can anneal to any complementary region on the exposed single stranded DNA template in a manner akin to random hexamer priming, but importantly, strand extension will only occur where the 3'-end has annealed with absolute complementarity. Since the 3'-ends of the oligos in the mixture are designed to be complementary to stop codons, only when the 3'-end of an oligo has bound specifically to the matching stop codon will primer extension and subsequent PCR amplification occur. Binding to out-of-frame stop codons and those downstream of the true stop codon of the gene of interest will also occur, resulting in the PCR amplification of not only the exact, full-length gene but also a set of truncated and extended products. However, these can easily be screened out in subsequent steps because they will not give rise to in-frame fusions to the peptide tag.

Carrying out the annealing and extension procedure on a nested set of 5'-deletions as described has significant advantages over carrying out an annealing and extension procedure on an entirely single stranded DNA or RNA molecule spanning an entire coding region. This is because the number of sites to which the primers can anneal specifically prior to extension is greatly restricted by the presence of the double strand portion of the nested set of deletions. The single strand portion of the nested set of deletions will span mainly the 3'-untranslated region of the genes and this will have the effect of strongly biasing the extension products in favour of stop codons external to the coding sequence and also in favour of longer extension products; these factors will act to greatly increase the frequency with which the first in-frame stop codon is specifically removed by the overall procedure. Indeed we have attempted to anneal and extend the oligos described in step (b) below using an entirely single-stranded coding region template, and we were unable to identify any correctly modified, full-length clones from that experiment. By comparison, the results of the procedure described in detail below demonstrate clearly that use of the nested set of 5'-deletions as the template for the annealing and extension steps is both effective and efficient in facilitating the specific removal of the first in-frame stop codon of the coding sequence to yield full-length, in-frame fusions to the polypeptide tag.

(a) PCR Amplification and Exonuclease Digestion of Genes Prior to Tagging

Thus, we first carried out an initial PCR amplification of a GST gene exactly as described in Example 1, steps (a) and (b), except that the 'STreverse' primer in the amplification was now 5'-phosphorylated. The purified PCR product was then digested with 2.5 units of λ exonuclease (Novagen Strandase kit) for 40 minutes at 37° C. in a standard reaction buffer (67 mM glycine-KOH pH9.4, 2.5 mM $MgCl_2$, 50 µg/ml bovine serum albumin). The enzyme was then inactivated by heating to 75° C. for 15 minutes. Since the λ exonuclease enzyme only recognises 5'-phosphate groups as substrates, the sense strand is protected from digestion and the product of the digestion is therefore a nested set of deletions from the 5'-end of the antisense strand of the PCR product.

(b) Specific Ligation, Extension and Amplification to Introduce Tag

5 µl of the λ exonuclease reaction mix was diluted into *E. coli* DNA polymerase I reaction buffer in the presence of 250 µM dNTPs and an ~25-fold molar excess of the following degenerate oligo set:

5'-GTA AAA CGA CGG CCA GTC TGG AGG AGG AGA NNN NNN TCA-3' (SEQ ID NO: 25)

The digested fragments and the oligos were annealed for 30 minutes at 37° C. and then 5 units of *E. Coli* DNA polymerase I were added after which the reaction was incubated for 3 hours at 37° C. The extended products were purified using a QIAquick PCR cleanup kit (Qiagen) under standard conditions and used as template in a standard PCR reaction using Pwo polymerase with primers 'STforward' and 'LMB2'. 30 cycles of PCR (94° C., 1 min; 57° C. 1 min; 72° C. 2 min) were carried out to generate PCR products ranging up to 1000 bp.

The PCR products generated from the above procedure were digested and cloned into the vector pMM106H as described in step (e) of Example 1. Colonies obtained from the cloning procedure were visualised at 365 nm to identify green fluorescent colonies. 73 such colonies were picked, replica-plated and analysed by colony Western blot under standard conditions using anti-His-tag and anti-GST antibodies. 58% of the green fluorescent colonies expressed protein which was positively recognised by both anti-His-tag and anti-GST antibodies. The DNA from 15 colonies which were both anti-His and anti-GST positive was amplified, purified and sequenced. The sequencing data confirmed the presence of 10 perfect in-frame fusions to full length GST, i.e. clones in which the first in-frame stop codon of the original GST gene had been specifically excised and replaced by an in-frame polyasparagine, hexahistidine tag. The rate of successful modification we obtained via this overall procedure is therefore 39% of the total number of green fluorescent colonies.

EXAMPLE 5

(a) Identification of One Protein from a Pool of 11 Genes

We have applied the procedure exactly as described in Example 1 except where specified to the pool of 11 different genes listed in the table below. We have generated arrays of the resultant specifically modified proteins such that each position in the array corresponds to a single recombinant protein immobilised through the tag appended as a result of this procedure. We have then screened the array by functional assay and have successfully identified individual protein components of the pool.

TABLE 1

Size and function of the eleven genes in the pool

| Gene | Size | Source and Function |
|---|---|---|
| glutathione S transferase | 950 bp | bacterial; detoxification |
| NF-κB p50 | 1165 bp | human; transcription factor |
| maltose binding protein | 1325 bp | bacterial; carbohydrate transport |
| alanine racemase | 1342 bp | bacterial; cell wall biosynthesis |
| nuclear factor of activated T cells (NFAT) | 1087 bp | murine; transcription factor |
| indoleglycerolphosphate synthase | 1528 bp | bacterial; amino acid biosynthesis |
| phosphoribosylanthranilate isomerase | 920 bp | bacterial; amino acid biosynthesis |
| tryptophan synthase (α-subunit) | 1122 bp | bacterial; amino acid biosynthesis |
| chymotrypsin inhibitor 2 | 389 bp | barley; serine protease inhibitor |
| peanut agglutinin | 1096 bp | peanut; carbohydrate binding |
| β-lactamase | 1040 bp | bacterial; antibiotic resistance |

Initially, all eleven genes were subcloned in to the same pTrcHisA vector backbone since amongst other things this mimics the situation encountered with a cDNA library. The primers 'STforward' and 'STreverse' described in Example 1 were designed to be universal primers for the amplification of genes encoded within a pTrcHisA vector 10 backbone.

The primer 'STforward' was designed such that it encodes a number of restriction sites as follows:

```
5'-ATG CTG ACG TCA TGAGGC CCA TGG GGC CCG GAT AAC AAT TTC ACA CAG G-3'
(SEQ ID NO: 3)

Aat II  Bsp HI      Sfi I
```

Thus, either of the restriction enzymes Aat II or Sfi I can be used to generate 3'-overhangs for exonuclease protection purposes. For directional cloning purposes at the end of the modification procedure, in this Example we chose to use Bsp HI since although statistically it will cut more frequently within a library, it generates cohesive ends which are compatible with the Nco I cloning site in the tag vector pMM106H used here and does not cut within any of the 11 genes in the present pool. Clearly, in principle any of the primer encoded restriction sites could be used providing that the tag vector contains an equivalent cloning site downstream of the promoter; Sfi I would have significant advantages in this regard in a larger library format because it has an 8 bp recognition sequence so the frequency of random occurrence of an Sfi I site within a given gene will be much lower (1 in $6.5 \times 10^4$) than that for a 6 bp recognition sequence such as that of Bsp HI (1 in 4,096).

The tag vector pMM106H is an 'ATG' vector, i.e. the 5'-cloning site (Nco I) overlaps the ATG start codon positioned downstream of a ribosome binding site (RBS) for expression of native proteins. However, in the procedure described here we are not reliant on the cloned genes having a common restriction site at their start codons. Instead, we simply rely on the vector-encoded promoter initiating transcription to produce mRNA, with the requisite signals for translational initiation being provided by the cloned genes themselves. Thus in this Example, all the genes in the original pool have a start codon immediately preceded by an RBS, irrespective of the presence or absence of a cloning site at the ATG. Since the primer 'STforward' binds upstream of the RBS in all eleven initial clones, subsequent post-modification cloning using any of the primer encoded restriction sites will introduce the newly modified genes in to the tag vector together with their original RBS and ATG so translation initiation will be ensured. In a cDNA library format, the same situation applies in that all full-length cDNAs will have their own 5'-untranslated regions (UTR) which contain the eukaryotic translational initiation signals. All that is required to obtain proper translational initiation in this case then is to clone the modified cDNA together with its 5'-UTR in to a eukaryotic vector which provides transcriptional initiation signals so once again; an equivalent universal set of PCR primers to those used in this Example could therefore be used.

The modification procedure was carried out as described in Example 1 with the following modifications. An equimolar pool of all eleven genes was used as the template for initial PCR amplification using primers 'STforward' and 'STreverse', after which fragments were digested with Sfi I to protect the 5'-end, since this enzyme has an 8 bp recognition sequence and does not cut within any of the 11 genes. Oligomix A (see Example 1) was used in the annealing step. After the second PCR amplification, modified fragments were divided into 2 pots which were digested separately with Bpm I and Sap I. Statistically a small fraction of genes in any library will contain either a Sap I site (7 bp recognition sequence; probability of random occurrence=1 in 16,384) or a Bpm I site (6 bp recognition sequence; probability of random occurrence=1 in 4,096) but only a very much smaller fraction will contain both (probability of random occurrence=1 in $6.7 \times 10^7$). The two Type II restriction enzymes were thus used separately to effectively ensure that the specific modification of any given full-length gene was not precluded by the presence of one or other restriction site within that gene.

Digested fragments from the two pots were then pooled for treatment with mung bean nuclease and digestion with Bsp HI. The resulting fragments were gel purified in 4 different size ranges and ligated separately to the vector pMM106H (itself digested to completion with Nco I and Hpa I and gel purified) in order to avoid preferential ligation of smaller inserts. Transformed cells were visualised under UV light (365 nm) and colonies which fluoresced green were selected by eye for analysis by Western blot. Approximately 30% of the total number of transformed colonies fluoresced green of which, 73% expressed proteins which are recognised by anti-His tag antibodies. 190 green, His-positive colonies were inoculated into 1.5 ml of liquid medium in 96-deep-well blocks and grown overnight. Cells were harvested by centrifugation and lysed by freeze-thaw/lysozyme. The crude lysates were then applied to individual wells of a Nickel-NTA-coated 96-well plate and unbound proteins were removed by washing, leaving the His tagged recombinant proteins immobilised in the wells. The immobilised proteins were then assayed for NF-κB activities using the assay described in Example 2 and wells containing positive 'hits' were identified by the appearance of yellow colouration. Three clones showed positive 'κB-motif' DNA binding activity. Further characterisation of the positive clones showed that one encoded a precise, full-length in-frame fusions of the NF-κB p50 gene to the hexahistidine tag as expected. The other two clones were found to encode related DNA binding proteins which are known to share the same DNA binding specificity as NF-κB p50, albeit with lower binding affinities.

This result therefore demonstrates that functional interrogation of arrays generated by this procedure can identify both specific interactions and also weaker interactions which are nonetheless specific and biologically relevant. We have therefore used this procedure to create arrays of functional proteins in a microwell format and using these arrays we have successfully identified individual proteins from a small pool based on a specific protein-ligand interaction.

The invention claimed is:

1. A method of generating a protein array from a library of two or more non-identical target DNA sequences the method comprising:
   (a) inserting a marker DNA sequence in frame immediately following a start codon of each of the target DNA sequences or immediately preceding a stop codon of each of the target DNA sequences or both, to form a library of modified DNA sequences which encode a library of modified amino acid sequences each comprising a marker moiety;
   (b) expressing the library of modified target amino acid sequences from the library of modified DNA sequences;
   (c) immobilizing to a single support in a single step the library of two or more modified target amino acids sequences from lysate, and wherein the marker moieties of the target modified amino acid sequences are attached to the single support in a spatially defined format, thereby generating a protein array, and
   (d) washing said solid support to remove unbound proteins, thereby generating an array of purified proteins.

2. The method as claimed in claim 1 wherein the marker moiety is a peptide sequence selected from the group consisting of:
   (a) a histidine tag;
   (b) a complete protein or protein domain;
   (c) a maltose binding protein domain;
   (d) an antibody epitope;
   (e) biotin or a biotin mimic;
   (f) a glutathione-S-transferase (GST) domain; and
   (g) a peptide sequence which effects attachment to the solid support.

3. The method of claim 2 wherein the marker moiety is selected from the group consisting of FLAG and Strep.

4. The method as claimed in claim 1 wherein the marker moiety allows for purification of the individual proteins in the array.

5. The method of claim 1 wherein the marker DNA sequence is inserted such that the start or stop codon for each of the proteins is replaced.

6. A method of screening one or more compounds for biological activity which comprises:
   (a) bringing said one or more compounds into contact with the array made according to any one of claims 1 to 5; and
   (b) measuring binding of the one or more compounds to the proteins in the array.

7. A method of screening one or more proteins for specific protein-protein interactions which comprises the step of bringing said one or more proteins into contact with an array made according to any one of claims 1 to 5, and measuring binding of the one or more specific proteins with the proteins of the array.

8. A method of screening one or more proteins for specific interactions with one or more nucleic acid probes which comprises the step of bringing said one or more nucleic acid probes into contact with an array made according to any one of claims 1 to 5, and measuring binding of the probes to the proteins in the array.

9. A method for the rapid screening of a test compound, test protein or test nucleic acid, the method comprising:
   (a) contacting the test compound, test protein or test nucleic acid with a spatially defined array produced according to any one of claims 1-5 comprising a plurality of array bound proteins, with each array bound protein being at a different position on a solid support, wherein the plurality of array bound proteins comprises a plurality of different proteins expressed in a single species; and
   (b) detecting any interaction between the array bound proteins and the test compound, test protein or test nucleic acid.

10. A method of screening for molecules which recognize each protein in the array, the method comprising:
    (a) contacting the molecules with a spatially defined array comprising a plurality of array bound proteins produced according to any one of claims 1-5, with each array bound protein being at a different position on a solid support, wherein the plurality of array bound proteins comprises a plurality of different proteins expressed in a single species; and
    (b) detecting any interaction between the array bound proteins and the molecules.

11. A method of generating an antibody array which comprises
    (a) bringing a protein array, made according to any one of claims 1 to 5, into contact with an antibody library, such that one or more proteins in the protein array bind to at least one antibody in the antibody library;
    (b) removing any unbound antibodies; and
    (c) immobilisation of those antibodies bound to proteins in the protein array.

12. A method for the screening of protein function or abundance which comprises the step of bringing an antibody array as defined in claim 11 into contact with a mixture of one or more proteins.

13. The method of any one of claims 1 to 5 wherein the protein array comprises serine proteases, kinases or p450 enzymes.

14. The method of any one of claims 1 to 5 wherein said library of modified amino acid sequences are modified human amino acid sequences.

15. The method of claim 1 or 2 wherein the marker moiety is post-translationally modified.

16. The method of claim 15 wherein the post-translational modification comprises the addition of a biotin or a lipid molecule.

17. The method of claim 1 wherein said modified amino acid sequences are folded into the correct conformation.

18. The method of claim 1 wherein said inserting step inserts a marker DNA sequence in frame immediately following a start codon of each target DNA sequence and immediately preceding a stop codon of each target DNA sequence, to form a library of modified DNA sequences which encode a library of modified amino acid sequences each comprising two marker moieties.

19. A method of generating a proteomic array of proteins of unknown amino acid sequences comprising the steps of:
   (a) providing a cDNA library as a plurality of target DNA sequences; and
   (b) generating a protein array using the method of any of claims 1 to 5 to produce a proteomic array of proteins of unknown amino acid sequence.

20. A method of screening for antibodies which recognize each protein in the array, the method comprising:
   (a) contacting the antibodies with a spatially defined array comprising a library of array bound proteins produced according to any one of claims 1-5, with each array bound protein being at a different position on a solid support, wherein the library of array bound proteins comprises a library of different proteins expressed in a single species; and
   (b) detecting any interaction between the array bound proteins and the antibodies.

21. The method of claim 1, wherein the marker moiety provides a high-affinity attachment to the solid support.

* * * * *

SEQUENCE LISTING

<160> NUMBER OF SEQ ID NOS: 25

<210> SEQ ID NO 1
<211> LENGTH: 41
<212> TYPE: DNA
<213> ORGANISM: Artificial Sequence
<220> FEATURE:
<223> OTHER INFORMATION: Primer

<400> SEQUENCE: 1
atgctgcaga cgtcaacagt atccatggcc cctatactag g         41

<210> SEQ ID NO 2
<211> LENGTH: 36
<212> TYPE: DNA
<213> ORGANISM: Artificial Sequence
<220> FEATURE:
<223> OTHER INFORMATION: Primer

<400> SEQUENCE: 2
gcgaggaagc ttgtcaatca gtcacgatga attccc              36

<210> SEQ ID NO 3
<211> LENGTH: 49
<212> TYPE: DNA
<213> ORGANISM: Artificial Sequence
<220> FEATURE:
<223> OTHER INFORMATION: Primer

<400> SEQUENCE: 3
atgctgacgt catgaggccc atggggcccg gataacaatt tcacacagg    49

<210> SEQ ID NO 4
<211> LENGTH: 34
<212> TYPE: DNA
<213> ORGANISM: Artificial Sequence
<220> FEATURE:
<223> OTHER INFORMATION: Primer

<400> SEQUENCE: 4
gcggatcctt gcggccgcca ggcaaattct gttt                34

<210> SEQ ID NO 5
<211> LENGTH: 39
<212> TYPE: DNA
<213> ORGANISM: Artificial Sequence
<220> FEATURE:
<223> OTHER INFORMATION: Primer

<400> SEQUENCE: 5
taaggaagag ctagtactcc agactggccg tcgttttac           39

<210> SEQ ID NO 6
<211> LENGTH: 39
<212> TYPE: DNA
<213> ORGANISM: Artificial Sequence
<220> FEATURE:
<223> OTHER INFORMATION: Primer

<400> SEQUENCE: 6
taaagaagag ctagtactcc agactggccg tcgttttac           39

<210> SEQ ID NO 7
<211> LENGTH: 39

<212> TYPE: DNA
<213> ORGANISM: Artificial Sequence
<220> FEATURE:
<223> OTHER INFORMATION: Primer

<400> SEQUENCE: 7
taatgaagag ctagtactcc agactggccg tcgttttac                          39

<210> SEQ ID NO 8
<211> LENGTH: 39
<212> TYPE: DNA
<213> ORGANISM: Artificial Sequence
<220> FEATURE:
<223> OTHER INFORMATION: Primer

<400> SEQUENCE: 8
taacgaagag ctagtactcc agactggccg tcgttttac                          39

<210> SEQ ID NO 9
<211> LENGTH: 39
<212> TYPE: DNA
<213> ORGANISM: Artificial Sequence
<220> FEATURE:
<223> OTHER INFORMATION: Primer

<400> SEQUENCE: 9
tagggaagag ctagtactcc agactggccg tcgttttac                          39

<210> SEQ ID NO 10
<211> LENGTH: 39
<212> TYPE: DNA
<213> ORGANISM: Artificial Sequence
<220> FEATURE:
<223> OTHER INFORMATION: Primer

<400> SEQUENCE: 10
tagagaagag ctagtactcc agactggccg tcgttttac                          39

<210> SEQ ID NO 11
<211> LENGTH: 39
<212> TYPE: DNA
<213> ORGANISM: Artificial Sequence
<220> FEATURE:
<223> OTHER INFORMATION: Primer

<400> SEQUENCE: 11
tagtgaagag ctagtactcc agactggccg tcgttttac                          39

<210> SEQ ID NO 12
<211> LENGTH: 39
<212> TYPE: DNA
<213> ORGANISM: Artificial Sequence
<220> FEATURE:
<223> OTHER INFORMATION: Primer

<400> SEQUENCE: 12
tagcgaagag ctagtactcc agactggccg tcgttttac                          39

<210> SEQ ID NO 13
<211> LENGTH: 39
<212> TYPE: DNA
<213> ORGANISM: Artificial Sequence
<220> FEATURE:
<223> OTHER INFORMATION: Primer

<400> SEQUENCE: 13
tgaggaagag ctagtactcc agactggccg tcgttttac                                    39

<210> SEQ ID NO 14
<211> LENGTH: 39
<212> TYPE: DNA
<213> ORGANISM: Artificial Sequence
<220> FEATURE:
<223> OTHER INFORMATION: Primer

<400> SEQUENCE: 14
tgaagaagag ctagtactcc agactggccg tcgttttac                                    39

<210> SEQ ID NO 15
<211> LENGTH: 39
<212> TYPE: DNA
<213> ORGANISM: Artificial Sequence
<220> FEATURE:
<223> OTHER INFORMATION: Primer

<400> SEQUENCE: 15
tgatgaagag ctagtactcc agactggccg tcgttttac                                    39

<210> SEQ ID NO 16
<211> LENGTH: 39
<212> TYPE: DNA
<213> ORGANISM: Artificial Sequence
<220> FEATURE:
<223> OTHER INFORMATION: Primer

<400> SEQUENCE: 16
tgacgaagag ctagtactcc agactggccg tcgttttac                                    39

<210> SEQ ID NO 17
<211> LENGTH: 39
<212> TYPE: DNA
<213> ORGANISM: Artificial Sequence
<220> FEATURE:
<223> OTHER INFORMATION: Primer
<221> NAME/KEY: misc_feature
<222> LOCATION: (4)..(9)
<223> OTHER INFORMATION: n= a or g or t or c

<400> SEQUENCE: 17
taannnnnna ctcctcctcc agactggccg tcgttttac                                    39

<210> SEQ ID NO 18
<211> LENGTH: 39
<212> TYPE: DNA
<213> ORGANISM: Artificial Sequence
<220> FEATURE:
<223> OTHER INFORMATION: Primer
<221> NAME/KEY: misc_feature
<222> LOCATION: (4)..(9)
<223> OTHER INFORMATION: n= a or g or t or c

<400> SEQUENCE: 18
tagnnnnnna ctcctcctcc agactggccg tcgttttac                                    39

<210> SEQ ID NO 19
<211> LENGTH: 39
<212> TYPE: DNA
<213> ORGANISM: Artificial Sequence
<220> FEATURE:
<223> OTHER INFORMATION: Primer
<221> NAME/KEY: misc_feature
<222> LOCATION: (4)..(9)
<223> OTHER INFORMATION: n= a or g or t or c

<400> SEQUENCE: 19
tgannnnnna ctcctcctcc agactggccg tcgttttac                                39

<210> SEQ ID NO 20
<211> LENGTH: 31
<212> TYPE: DNA
<213> ORGANISM: Artificial Sequence
<220> FEATURE:
<223> OTHER INFORMATION: Primer

<400> SEQUENCE: 20
cgtatgttgt ggggaattcc cagcggataa c                                        31

<210> SEQ ID NO 21
<211> LENGTH: 31
<212> TYPE: DNA
<213> ORGANISM: Artificial Sequence
<220> FEATURE:
<223> OTHER INFORMATION: Primer

<400> SEQUENCE: 21
gttatccgct gggaattccc cacaacatac g                                        31

<210> SEQ ID NO 22
<211> LENGTH: 39
<212> TYPE: DNA
<213> ORGANISM: Artificial Sequence
<220> FEATURE:
<223> OTHER INFORMATION: Primer
<221> NAME/KEY: misc_feature
<222> LOCATION: (31)..(36)
<223> OTHER INFORMATION: n= a or g or t or c

<400> SEQUENCE: 22
gtaaaacgac ggccagtctg gaggaggaga nnnnnntca                                39

<210> SEQ ID NO 23
<211> LENGTH: 39
<212> TYPE: DNA
<213> ORGANISM: Artificial Sequence
<220> FEATURE:
<223> OTHER INFORMATION: Primer
<221> NAME/KEY: misc_feature
<222> LOCATION: (31)..(36)
<223> OTHER INFORMATION: n= a or g or t or c

<400> SEQUENCE: 23
gtaaaacgac ggccagtctg gaggaggaga nnnnnntta                                39

<210> SEQ ID NO 24
<211> LENGTH: 39
<212> TYPE: DNA
<213> ORGANISM: Artificial Sequence
<220> FEATURE:
<223> OTHER INFORMATION: Primer
<221> NAME/KEY: misc_feature
<222> LOCATION: (31)..(36)
<223> OTHER INFORMATION: n= a or g or t or c

<400> SEQUENCE: 24
gtaaaacgac ggccagtctg gaggaggaga nnnnnncta                                39

<210> SEQ ID NO 25
<211> LENGTH: 39
<212> TYPE: DNA
<213> ORGANISM: Artificial Sequence
<220> FEATURE:

```
-continued

<223> OTHER INFORMATION: Primer
<221> NAME/KEY: misc_feature
<222> LOCATION: (31)..(36)
<223> OTHER INFORMATION: n= a or g or t or c

<400> SEQUENCE: 25
gtaaaacgac ggccagtctg gaggaggaga nnnnnntca                              39
```